June 8, 1943. J. W. ROBINSON Plant Pat. 589
CAMELLIA PLANT
Filed Nov. 28, 1941
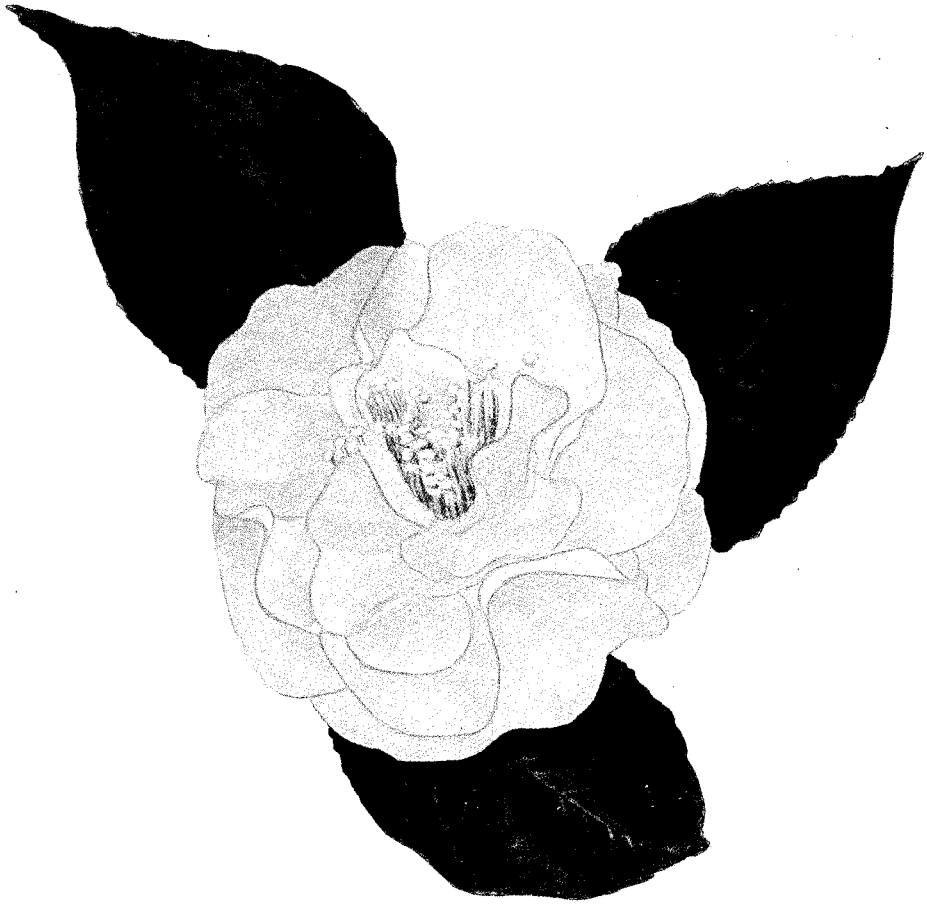
INVENTOR.
BY J. W. Robinson
A. Schapp
Attorney Patented June 8, 1943

Plant Pat. 589

UNITED STATES PATENT OFFICE

589

CAMELLIA PLANT

James W. Robinson, Richmond, Calif.

Application November 28, 1941, Serial No. 420,873

1 Claim. (Cl. 47—60)

The present invention relates to a new and distinct variety of camellia plant, and comprises a natural hybrid, and its principal characteristic is a fragrance similar to that of a wild rose.

I have asexually reproduced this new variety of camellia plant by grafting in the spring of 1941.

The accompanying drawing shows a specimen of my new variety of camellia plant viewing it from above and in approximately its true and exact color.

A detailed and true description of my new variety of camellia plant follows:

Parentage: A natural hybrid.

Classification: Botanic—large flowered; derived from the species *Camellia japonica*; commercial—semi-double.

Blooming habits: Observations made in the field of James W. Robinson, at Richmond, California, at noon of February 22, 1941, disclosed the following characteristics:

*Size.*—Medium size of three to three and one-half and occasionally four inches in diameter.

*Form.*—Deep of good substance, lasting from ten days to two weeks, when cut.

*Color.*—Rich, deep pink, all petals one color, pollen yellow, leaves willow-green of medium texture and inclined to be slightly wavy, stammens sometimes showing a trace of red.

*Petals.*—Usually from eighteen to twenty in number.

*Fragrance.*—Moderate, quite similar to that of an old-fashioned wild rose. When the flower first opens, no fragrance is noted; usually about the second or third day, after it comes into full bloom and the pollen is loose and the bees begin working on it, the fragrance has developed, this fragrance lasting several days if the bloom is not severed from the plant.

I claim:

A new and distinct variety of camellia plant, of the semi-double type, characterized as to novelty by its very pleasing fragrance, similar to that of a wild rose, by its rich, deep pink and uniform color, by the medium texture of the willow-green leaves inclined to be slightly wavy, and by a flower about three to three and one-half inches in diameter, of considerable depth and lasting from ten days to two weeks when cut, substantially as shown and described.

JAMES W. ROBINSON.